United States Patent [19]

Kaufman et al.

[11] 4,255,659

[45] Mar. 10, 1981

[54] SEMICONDUCTOR RADIATION DETECTOR

[75] Inventors: Leon Kaufman, San Francisco; Kenneth E. Hosier, Jr., Martinez, both of Calif.

[73] Assignee: The Regents of the University of California, Berkeley, Calif.

[21] Appl. No.: 890,841

[22] Filed: Mar. 27, 1978

[51] Int. Cl.² .............................................. G01T 1/22
[52] U.S. Cl. .................................. 250/370; 250/445 T
[58] Field of Search ................. 250/370, 445 T, 363 S, 250/369, 388; 307/200 R

[56] References Cited

U.S. PATENT DOCUMENTS

| 3,598,997 | 8/1971 | Baertsch | 357/29 |
|---|---|---|---|
| 3,624,399 | 11/1971 | Boer et al. | 357/29 |
| 4,034,223 | 7/1977 | Kowalski | 250/445 T |
| 4,055,766 | 10/1977 | Miller et al. | 250/370 |

FOREIGN PATENT DOCUMENTS

| 1015897 | 1/1966 | United Kingdom . |
| 1082960 | 9/1967 | United Kingdom . |
| 1095162 | 12/1967 | United Kingdom . |
| 1154825 | 6/1969 | United Kingdom . |
| 1351026 | 4/1974 | United Kingdom . |
| 1481166 | 7/1977 | United Kingdom . |

OTHER PUBLICATIONS

Kaufman et al., "Two-Detector, 512-Element High Purity Germanium Camera Prototype," IEEE Transactions on Nuclear Science, vol. NS-25, No. 1, Feb. 1978, pp. 189-195.

R. Allemond et al., "Present Limitations of CdTe Detectors in Nuclear Medicine," Revue de Physique Appliquee, T. 12, Feb. 1977, pp. 365-367.

G. A. Armantrout et al., "What Can Be Expected from High-Z Semiconductor Detectors?," IEEE Transactions on Nuclear Science, vol. NS-24, No. 1, Feb. 1977, pp. 121-125.

*Primary Examiner*—Davis L. Willis
*Attorney, Agent, or Firm*—Larry S. Nixon

[57] ABSTRACT

An electrical charge amplifier including a filter circuit is AC coupled to a semiconductor (CdTe) detector and generates a voltage pulse in response to an electrical charge generated in the detector by an incident pulse of radiation. The filter allows only frequencies within a predetermined range to contribute to the voltage pulse. The selected range of frequencies is determined in accordance with the duration of the incident radiation pulse such that the voltage pulse faithfully represents the magnitude of incident radiation in spite of undersirable detector characteristics which would otherwise introduce distortions. Exemplary charge amplifier and detector structures are also described.

59 Claims, 24 Drawing Figures

PULSED-MODE

| POSITION | ENERGY (NORMALIZED) |
|---|---|
| A | 989 |
| B | 984 |
| C | 825 |
| D | 966 |
| E | 959 |
| F | 1000 |
| G | 996 |
| H | 982 |
| I | 937 |

9A

9B

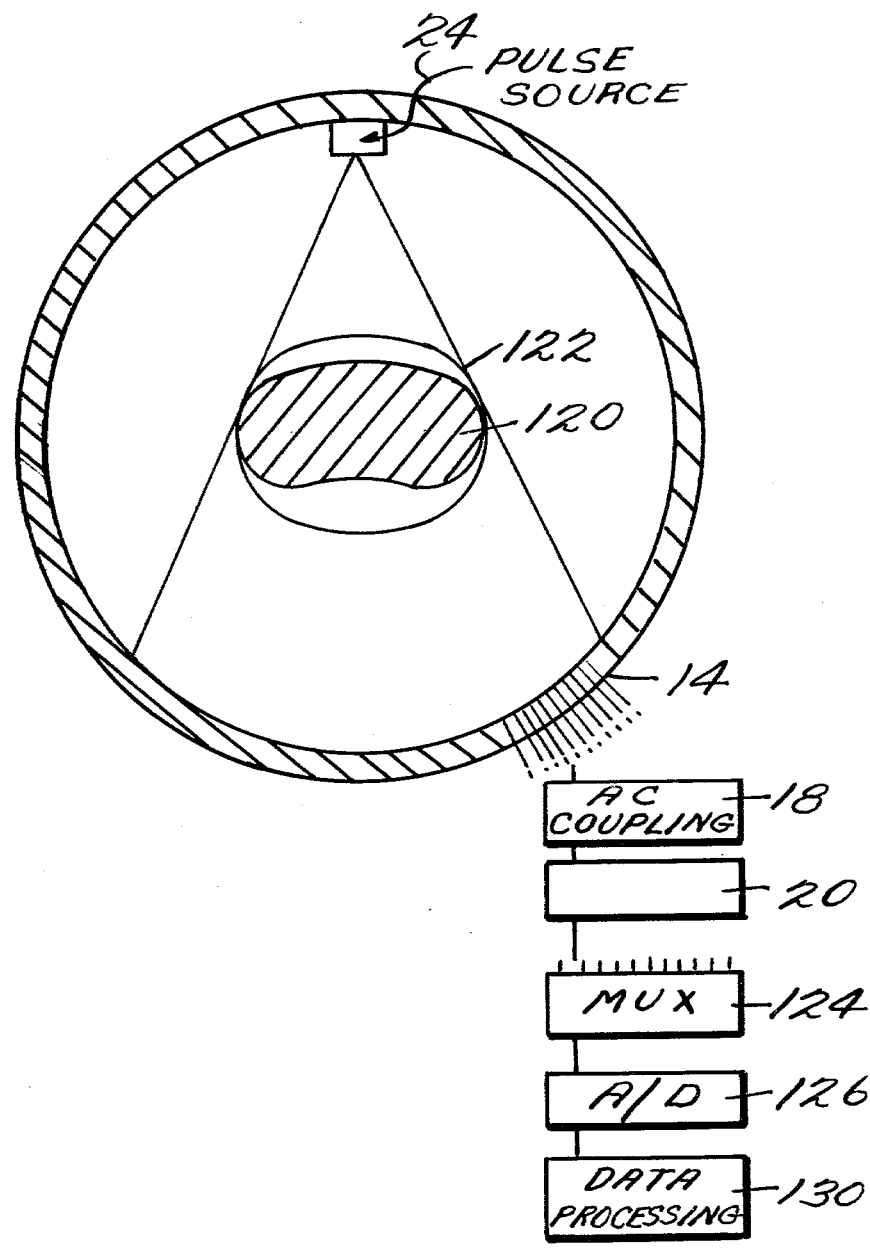

SEMICONDUCTOR RADIATION DETECTOR

FIELD OF THE INVENTION

The present invention generally relates to the use of semiconductor radiation detectors, and more particularly, to a cadmium telluride (CdTe) detector which is suitable for use in computerized tomographic (CT) X-ray scanning apparatus.

BACKGROUND OF THE INVENTION

There are many devices which now use radiation detectors. For example, CT scanning has proven invaluable for medical diagnosis and analysis and is now in wide use. However, the newest CT scanning techniques tend to be somewhat expensive, due in part to the cost of the components normally associated with a large number of radiation detectors.

CT scanners are utilized to provide a computed cross-sectional detail of soft living tissue structures. Briefly, the cross-section of interest is positioned between a radiation source (e.g., an X-ray tube) and a detector system. A portion of the beam is absorbed by the tissue during transit along ray paths through the section. Thus, absorption by the body section along any given path is a function of the sum of the absorption coefficients of the particular body tissues through which the beam passes. That portion of the radiation which passes through the section is detected by, for example, a scintillation crystal which produces light photons in response to incident radiation. Typically, the scintillator is optically coupled to a photomultiplier tube (PMT) which converts the light photons into electrical output signals. Such measurements are made along many paths through the body section to provide data used in calculating an array of point-by-point relative absorption coefficients. The computed coefficients are then utilized to provide a visual display of the cross-section.

Some of the earlier CT scanners obtain the requisite multiplicity of absorption measurements by synchronously scanning the body section with a highly collimated X-ray beam and an aligned single detector. The beam and detector are together translated to scan the body section and generate a set of measurements along parallel paths. This assembly is then rotated with respect to the body section and the translation-rotation operation is repeated to provide sets of measurements at different angular dispositions.

It is desirable, however, to minimize the overall scanning time. Accordingly, more recent CT scanners generally utilize a plurality of individual radiation detectors in co-operation with a fan-shaped X-ray beam wide enough to irradiate the entire body section. In one example of such systems, a fan-beam source rotates about the body section, irradiates a stationary detector array forming the outside perimeter of the scanning frame. As many as 600 scintillation crystals and associated photomultipliers tubes (PMT) are typically used in such systems. Thus, the cost of the scintillation crystal-PMT detectors, and particularly the photomultiplier tubes, presently represent a substantial portion of the cost of such CT scanners. Accordingly, it is desirable to directly convert the radiation to an electrical signal and eliminate the need for large numbers of photomultiplier tubes and associated circuits.

Various direct conversion detectors such as Xenon gas and high purity germanium (HPGe) semiconductors have been utilized in the past. However, such detectors are disadvantageous for other reasons.

The properties of high purity germanium are well known. A high density position sensitive array has been described in "Two Detector 512-Element High Purity Germanium Camera Prototype" Kaufman et al, IEEE Transactions Nuclear Science, NS-25, February, 1978. (Presently in press) However, the production of high purity germanium is a relatively complex and costly procedure, and further high purity germanium detectors require special cooling apparatus, (e.g. liquid nitrogen). Additionally, it is desirable in CT scanning applications to use a thinner detector than generally can be made with high purity germanium.

Room temperature semiconductor detectors would thus appear to be a natural choice for application in CT scanners. Since photon energy from the radiation is directly converted into an electrical charge, compact arrays could be assembled without the requirement of more bulky photomultiplier tubes. Such higher detection element density is especially advantageous for CT scanning applications. These high density semiconductor detector arrays could also be mass produced by batch processing.

However, semiconductor detector materials now available in reasonable quantities have been considered by others in the past and discounted as unsuitable for CT scanning applications. For example, cadmium telluride (CdTe) has specifically been studied with respect to use as a detector in nuclear medicine, and has been found not compatible with the needed accuracies. Specific reference is made to Allemand et al, "Present Limitations of CdTe Detectors in Nuclear Medicine", Revue de Physique Appliquee, 12: 365–367, February, 1977. Other semiconductor detectors are discussed in Armantrout et al, "What Can Be Expected from High-Z Semiconductor Detectors", IEEE Transactions on Nuclear Science, Vol. NS-24, No. 1, Feb. 1977. Of the semiconductor materials that are described, various ones have been tested and show unsuitable characteristics similar to CdTe. Computer studies project that similar properties are present in other semiconductor detectors—not presently tested.

More specifically, CdTe detectors have been found to exhibit adverse "leakage current", "Tailing", "polarization" and "memory" properties, which are generally considered to render CdTe unsuitable for CT scanning usages. Other detectors, such as $HgI_2$, have been found to exhibit similar properties.

The high "leakage current" property varies with temperature, and further, varies with time once bias has been applied to the detector. The "tailing" phenomenon causes the detector response to portray a monochromatic (single energy) source as having energies ranging all the way down to noise levels. "Tailing" increases as a function of the elapsed time after bias is applied to the detector. The "polarization" property is manifested by the most frequently encountered detector response (hereinafter termed the photo-peak) to a constant monochromatic source, shifting towards the low energy end of the spectrum. The "memory" property is manifested by a continued current flow after a pulse of incident radiation has ceased, sometimes with a time constant of hours.

Various techniques have been proposed for dealing with such adverse properties. However, the proposed techniques have tended to merely add to the complexity of the detector circuitry and, in fact, to introduce sources of errors that have made application of CdTe detectors in CT scanners impractical. For example, the high current leakage could be compensated by sampling the detector output just before the X-ray beam is activated to produce each pulse of incident radiation. However, such a scheme will compromise the signal-to-noise ratio of the system when absorption is high, as happens when the beam goes through bone. Pre and post measurement calibration techniques for memory and polarization compensation, similarly tend to add signal-to-noise problems. Further, polarization compensation techniques wherein the bias to the detectors is turned off between measurements, are inadequate due to hysteresis effects.

SUMMARY OF THE INVENTION

In accordance with the present invention, it has been found that room temperature semiconductor detectors, and in particular CdTe detectors, can be made compatible with CT scanning operations. The detector is used in cooperation with a pulsed radiation source and frequency filtering techniques are utilized in measuring the resulting pulse of electrical charge developed by the detector. Only selected frequencies within a predetermined range, chosen in accordance with the duration of incident radiation pulse, contribute to the output pulse. More specifically, such range of frequencies is preferably a narrow band of frequencies centered about a frequency approximately equal to the inverse of twice the radiation pulse duration.

It has also been found that plural individual detectors can be formed as a unitary array on a single CdTe or $H_gI_2$ wafer by merely providing plural electrically separated electrodes. Thus, CdTe or $H_gI_2$ detectors are particularly advantageous in that entire high density arrays can easily and quickly be formed by batch processing. Further, two dimensional arrays can be formed by providing a grid work of such electrodes. Moreover, a stacked array for taking measurements at a plurality of differing energy levels can be provided by disposing a multi-electrode detector such that the radiation is incident on a wafer surface transverse to the electrodes.

BRIEF DESCRIPTION OF THE DRAWINGS

A preferred exemplary embodiment of the present invention will hereinafter be discussed with reference to the following drawings wherein like designations denote like elements and:

FIGS. 9A and 9B illustrate the uniform response of the CdTe detector of FIG. 8 when used in accordance with the present invention;

FIG. 18 is a block diagram of a CT scanner utilizing detectors in accordance with the present invention.

DETAILED DESCRIPTION OF AN EXEMPLARY EMBODIMENT

Figure 1A:
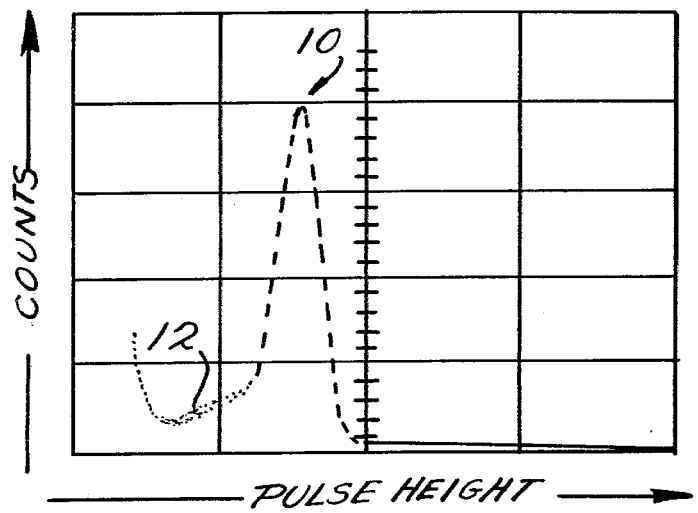
FIGS. 1A and 1B are spectral responses of CdTe detectors when used as in the prior art illustrating "tailing"
Figure 1B:
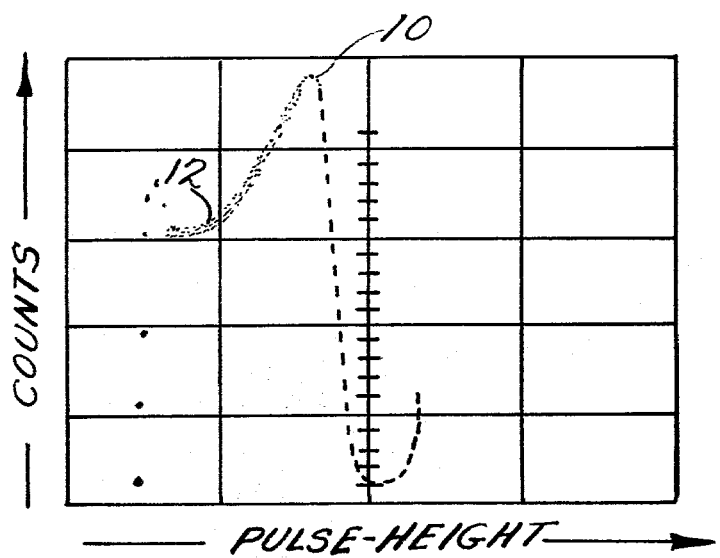

The present inventor has examined the properties of CdTe detectors by observing the spectral response the single photons from a monochromatic source (AM-241). FIGS. 1A and 1B illustrate the spectral response of two different CdTe detectors to a monochromatic source (AM-241) when used as in the prior art. Specifically, FIGS. 1A and 1B show the count of photons registered by the detector at various energy levels during a preset time interval, the energy level being indicated by the pulse height of the detector output.

Ideally, since the response was to a monochromatic source, all of the counts should have registered at a single energy providing a single impulse-like spike response. However, as illustrated in FIG. 1A, due to the tailing effect, the spectral response is broadened. Photons which should be depicted as counts at the photo-peak 10 (predominant energy level) are indicated as having energies ranging down to the noise level of the detector, and a plateau region 12 is manifested in the spectral response.

It is apparent from a comparison of FIGS. 1A and 1B, that the tailing effect is not uniform between individual detectors. The response shown in FIG. 1A is that of a relatively good (by prior art standards) CdTe detector, whereas the response shown in FIG. 1B of another CdTe detector to the same source evidences a worse peak-to-plateau ratio and poor energy resolution.

Figure 2:
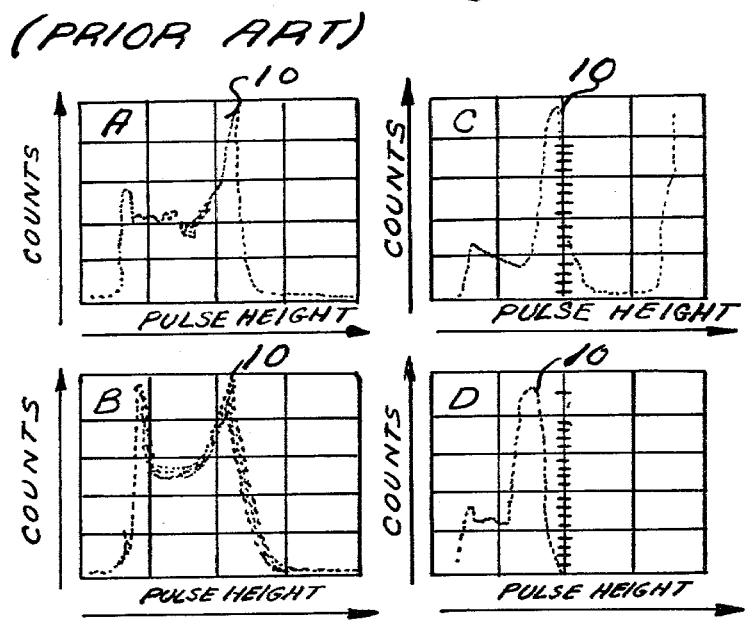
FIGS. 2A-2D are spectral response of CdTe detectors when used as in the prior art illustrating "polarization"

The polarization phenomenon shifts the photo-peak response toward the lower energy levels and the peak-to-plateau ratio decreases (a measure of the tailing effect) as a function of the time from the instant the detector is placed under bias is illustrated in FIGS. 2A—2D. FIGS. 2A and 2C show the spectral response of two different CdTe detectors to monochromatic AM-241 immediately after bias is applied. FIGS. 2B and 2D illustrate the spectral response of the respective detectors 15 minutes after bias is applied. It should be noted that the photo-peak 10 shifts towards the lower energy level, and the response widens as tailing increases. Such polarization has generally been attributed (apparently in error, as will be explained) to the loss of depletion depth with time. If such is the case, it follows that X-ray detection efficiency would be reduced as a function of time and since tailing worsens with time, the charge collection efficiency of the detector would also degrade with time. In any event, irrespective of the physics involved in a uncompensated detector, a steadily decreasing response to a steady X-ray source would be manifested.

Figure 3A:
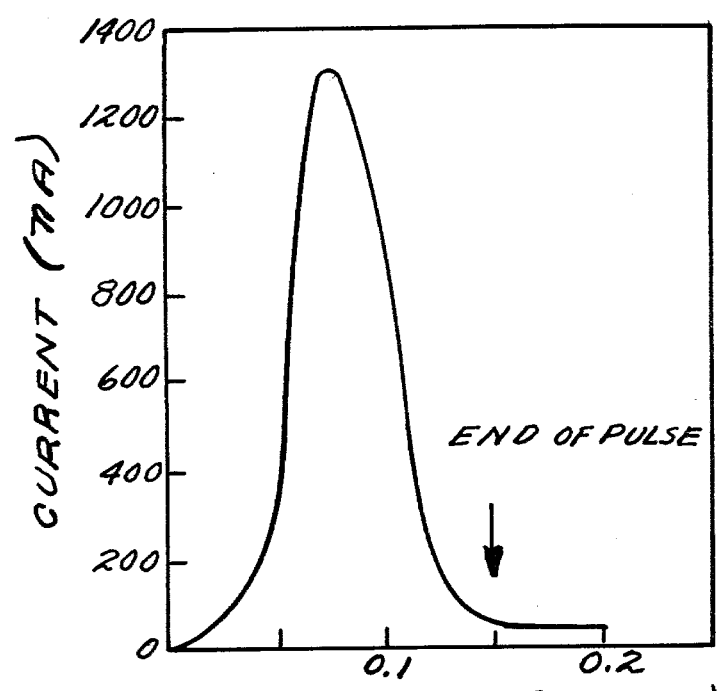
FIGS. 3A-3B are graphs illustrating "memory" of CdTe detectors when used as in the prior art.
Figure 3B:
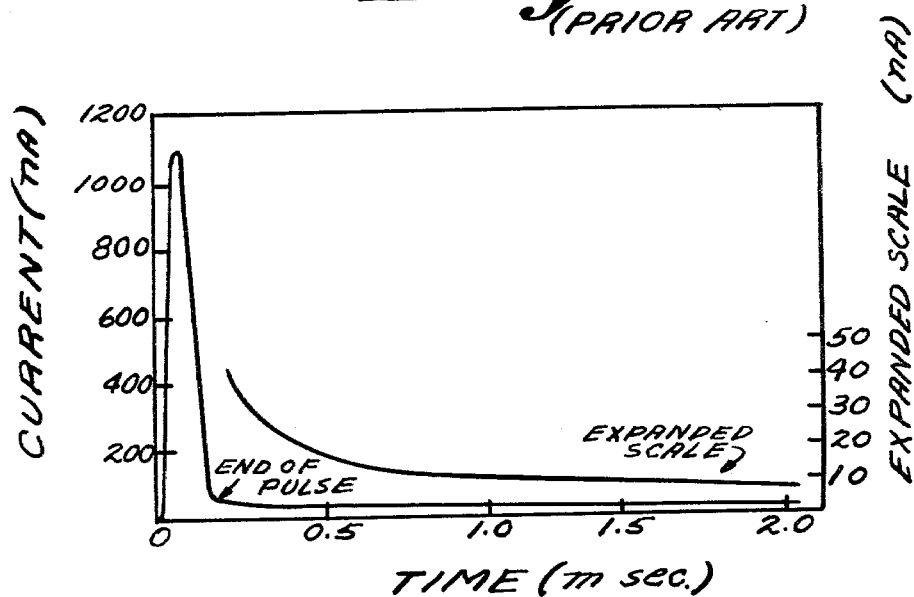

FIGS. 3A and 3B illustrate the memory property exhibited by CdTe detectors with current continuing to flow after an applied radiation pulse has terminated. More specifically, the current output of two different CdTe detectors are shown respectively in FIGS. 3A and 3B as a function of time, following exposure to a short X-ray pulse. It should be noted that leakage current does not decrease below 1% of maximum until approximately 25 μsec. and 800 μsec. after the end of the X-ray pulse for the respective detectors associated with FIGS. 3A and 3B. DC relaxation times were found to be approximately 0.5 minutes and 1.5 minutes respectively. Such memory phenomenon, absent compensation, would be unusable with CT scanners at present scanning rates.

Data is available which tends to indicate that the tailing effect is the result of the CdTe detector producing pulses of varying rise times. Reference in this regard is made to Jones, "the Use of CdTe γ Spectrometers in Monitoring Activity Deposited in Nuclear Power Stations", Revue de Physique Appliquee 12: 379–384, 1977. When processed with conventional amplifiers having Gaussian-shaped frequency responses, the varying rise times are manifested as pulses of different amplitudes. The above-noted Jones article appears to demonstrate that the fastest pulses correspond to photons of the highest energy level registered (the photo-peak) and that various bands in rise time correspond to energy bands in the tail.

While the polarization phenomenon is generally considered to be the result of a decreasing depletion depth, as noted above, the present inventor speculates that the polarization effect is the result of further degradation of rise time distributions during the period after bias is applied. Accordingly, polarization and tailing effects could effectively be eliminated if the detector is presented with a pulse of photons having a duration which is long compared to the longest detector rise times (approximately 1 μsec.). Thus, the pulse of radiation in effect drives the rise time response, and spurious signals not in accordance with the rise time of the pulse can be filtered from the detector output to provide an undistorted representation of the incident radiation pulse. Experimental results appear to verify this theory. In any event, irrespective of the physics of the phenomenon, the experimental results have proven that semiconductor detectors can be made compatible with the requisites of CT scanning when practiced in accordance with the present invention.

Figure 4:
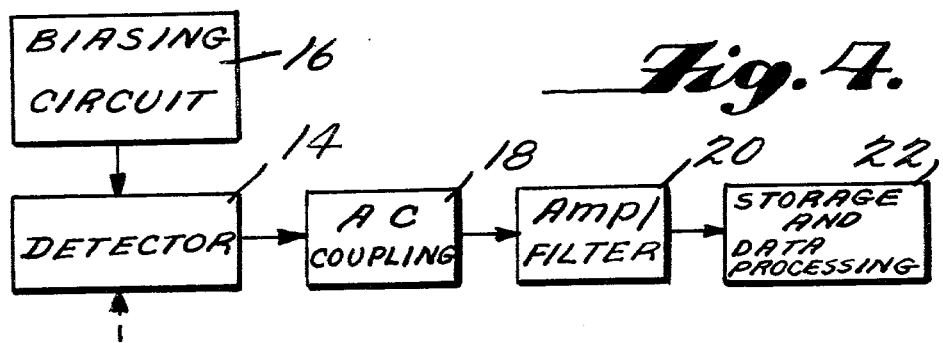
FIG. 4 is a block diagram of a radiation detecting system in accordance with the present invention.

With reference now to FIG. 4, a semiconductor detector 14 such as CdTe, suitably biased by circuitry 16, is AC coupled via means 18, (e.g., a capacitor), to an amplifier/filter 20. Amplifier/filter 20 is coupled to suitable storage and/or data processing means 22.

Figure 5:
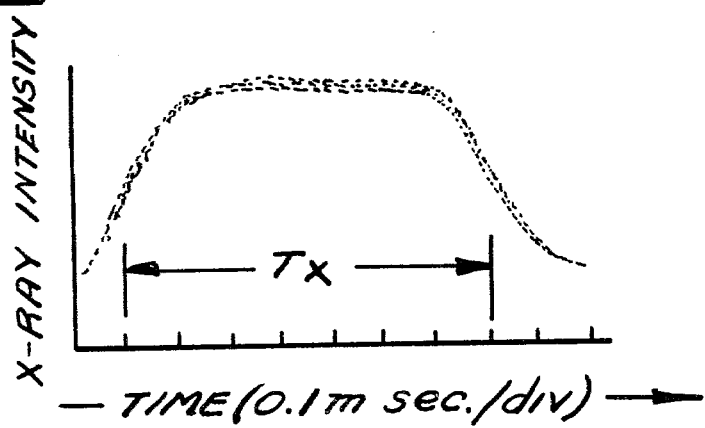
FIG. 5 represents the shape of a typical X-ray pulse.

Detector 14 cooperates with a pulsed radiation source 24. Source 24 can be a conventional pulse mode X-ray generator, or can be a constant source such as, for example, a Phillips MG160 X-ray generator, used in conjunction with a wheel chopper. Where wheel choppers are used, the rotational frequency of the wheel and ripple in the X-ray tube output signal tend to produce beats in pulse amplitude. Such beat frequencies can be compensated for by averaging a number of pulses. A typical X-ray pulse shape is shown in FIG. 5.

The effective time constant of biasing circuitry 16 and AC coupling 18 is chosen in accordance with the pulse repetition rate of source 24; the time constant being chosen to allow dectector 14 to recharge (recover) between radiation pulses.

Amplifier/filter 20 comprises means for generating a signal indicative of the charge developed by detector 14, and has a frequency response such that frequency components not within a predetermined range (band) of frequencies are effectively filtered from that signal. The predetermined frequency band is determined in accordance with radiation pulse duration and is preferably a narrow band of frequencies centered about a frequency approximately equal to the inverse of the radiation pulse duration or the inverse of twice the radiation pulse duration. For example, amplifier/filter 20 suitably comprises a charge sensitive first stage having a RC time constant TD, and a second stage having an effective RC time constant TS. It was found that by chosing the time constants such that TS is approximately equal to the duration of the X-ray pulse (TX) and much larger than TD, a strongly differentiated detector output pulse results, which provides faithful representation of the actual X-ray pulse shape. Accordingly, the integration of such a differentiated "X-ray pulse" yields an accurate indication of the total incident X-ray energy. Such an amplifier/filter will hereinafter be described in more detail in conjunction with FIG. 6.

In the alternative, the charge sensitive first stage can be made to have an RC time constant much larger than the duration TX of the X-ray pulse, and the second stage effectively shaping the first stage output by differentiation with time constant TD and integration with a time constant TS considerably shorter than TD but comparable to TX. Such a filtering amplifier (20B) will be more fully described in conjunction with FIGS. 10A and 10B. While such an arrangement successfully eliminates the effects of the detector characteristics from the output pulse it is often difficult to obtain adequate pole-zero compensation and tends to exhibit undesirable overshoot characteristics.

Figure 6:
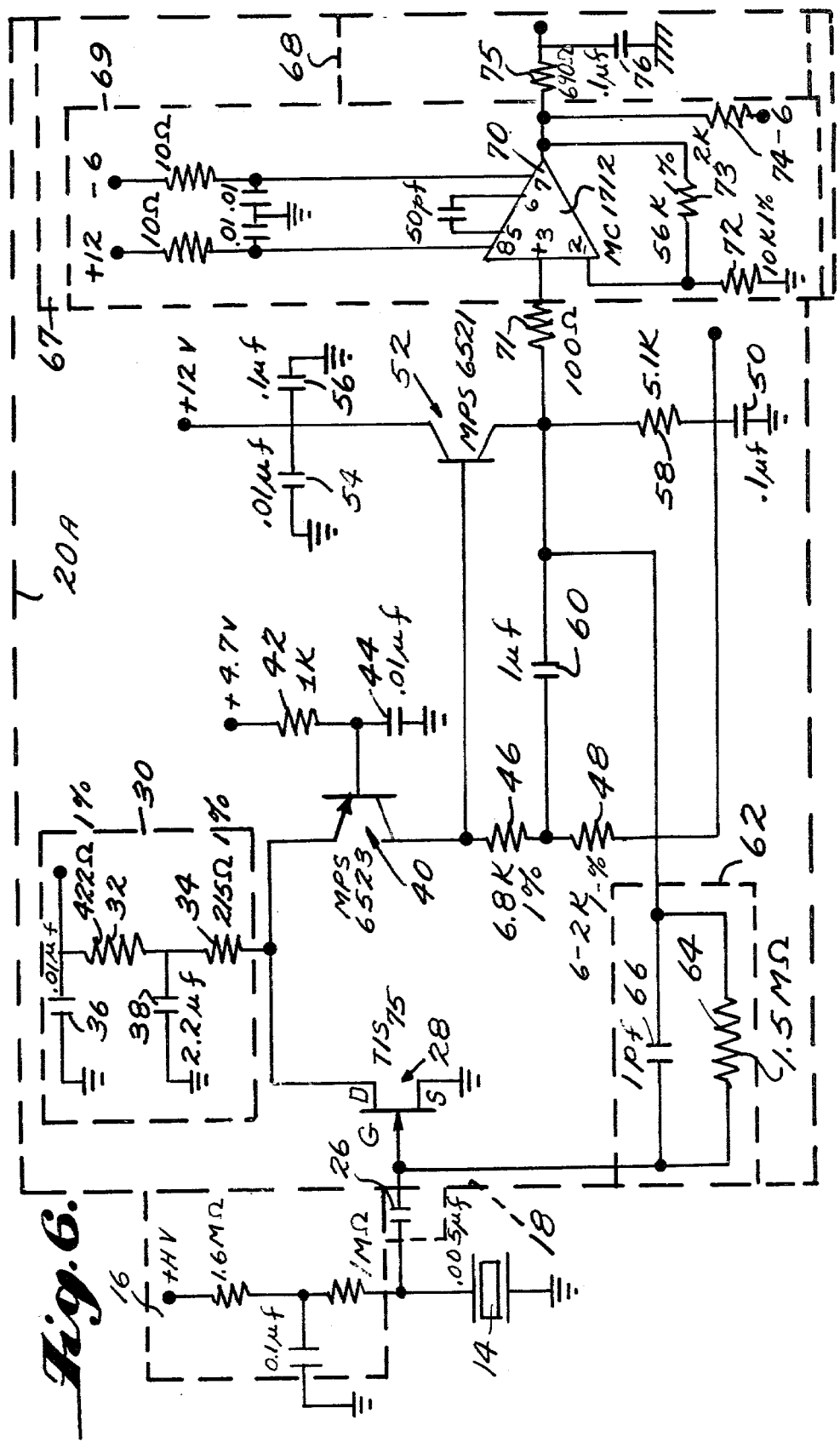
FIG. 6 is a schematic diagram of a suitable charge amplifier and filter means for use in the system of FIG. 4.

With reference now to FIG. 6, amplifier/filter 20A will now be described. Exemplary component values are given for use in conjunction with X-ray pulse durations on the order of 100 μsec.

A CdTe detector 14 is biased by a biasing circuit 16, and coupled through AC coupling means 18 to amplifier/filter 20A. AC coupling means 18 may be a 0.005 μf. capacitor 26. Capacitor 26 is coupled to the gate terminal of a field effect transistor 28, suitably of the type TIS 75, having grounded source and a drain suitably biased by a resistor-capacitor biasing network 30. Biasing network 30 may comprise resistors 32 (422Ω) and 34 (215Ω) serially connected between the source of FET 28 and a 24 volt source. Bypass capacitors 36 (0.1μf.) and 38 (212 μf.), are respectively coupled from the voltage source to ground and from the juncture between resistors 32 and 34 to ground.

The drain of FET 28 is also connected to the emitter of an PNP transistor 40 (e.g., of the type MPS 6523). The base of transistor 40 is coupled through a resistor 42 to a positive 4.7 volt source, and is AC coupled to ground through a capacitor 44 (0.01 μf.). The collector of transistor 40 is coupled through two serially connected resistors 46 and 48 to a negative 12 volt source. An AC bypass capacitor 50 is provided for the negative 12 volt source.

The collector of transistor 40 is also coupled to the base of an NPN transistor 52, (e.g., of the type MPS 6521). The collector of transistor 52 is connected to a positive 12 volt supply, the 12 volt supply being coupled to ground through each of two capacitors 54 (0.01 μf.) and 56 (0.1 μf.), respectively. The emitter of transistor 52 is coupled to the negative 12 volt source through a resistor 58 (5.1 KΩ). The emitter of transistor 52 is also connected through a capacitor 60 (1 μf.) to the juncture between resistors 46 and 48, (connected between transistor collector 40 and the negative 12 volt supply).

Additionally, a fast differentiator 62 is connected in a feedback loop between the emitter of transistor 52 and the gate of FET 28. Differentiator 62 may comprise a resistor 64, (1.5 MΩ), in parallel with a capacitor 66, (1 pf.).

The emitter of transistor 52 is also coupled to a second stage 67, comprising an integrator 68 preceded by a voltage amplifier 69. Voltage amplifier 69 suitably comprises a conventional operational amplifier (op amp) 70, for example, of the type MC1712. The emitter of transistor 52 coupled to the non-inverting input terminal of op amp 70 through a precision resistor 71 (100Ω). The inverting input terminal of op amp 70 is connected to ground potential through a precision resistor 72 (10KΩ), and feedback between the output terminal and inverting input terminal of op amp 70 is provided by a further precision resistor 73 (56KΩ). A connection is also made from the output terminal of op amp 70 to a negative 6 volt source through a resistor 74 (2K) to provide for generation of bipolar signals by amplifier 69. The output terminal of voltage amplifier 67 is connected to integrator 68, suitably comprising a resistor 75 (690Ω) and a capacitor 76 (0.1 μf.).

The circuit of FIG. 6 can be adapted for radiation pulse durations other than on the order of 100 μs, by adjusting the time constants of differentiator 62 and integrator 68. For example, the circuit can be made compatible with a 800 μs radiation pulse duration by adjusting the values of resistor 75 and capacitor 76 to increase the time constant of integrator 68 by a factor of 8 to 10.

A number of different detectors were tested in conjuction with the circuit of FIG. 6. The structure of such detectors will be discussed below. For comparison, the uncompensated signal photon characteristics of the detectors (as used in the prior art) were first noted. The results of the testing are shown in tabular form in TABLES I-V. Table I is a brief description of the individual detectors tested. The detector structures, per se, are conventional devices, except that in some instances the detectors are adapted, as will be explained, for operation with plural electrodes to form an array. Tables II and III show the uncompensated characteristics of the detectors, Table II shows the detector characteristics when bias voltage is first applied at the detector, and Table III shows the measurements taken 15 minutes after bias is applied.

TABLE I
DETECTOR SPECIFICATIONS

| Detector Code | Detector Model No. | Description | Electrodes |
|---|---|---|---|
| A1 | Radiation Monitoring Device (R.M.D.) NRD 0201 | Rectangular 2mm × 7mm × 2mm | Platinum (Pt)/Pt |
| A2 | M272-2 | Round (single electrode) 8mm Dia. × 2mm | Pt/Pt |
| A3 | M141-4 | Round (single electrode) 10mm Dia. × 2mm | Pt/aluminum-oxide O-Al (Pt. side neg.) (Purposely fabricated for poor results) |
| AA4 | NDO40-01 | Round (split electrode) 10mm Dia. × 2mm | Pt/Pt |
| AA5 | NDO40-02 | Round (split electrode) 10mm Dia. × 2mm | Pt/Pt |
| A6 | M353-4 | Rectangular 10mm × 15mm × 2mm (multi-electrode) | Pt/Pt |
| B7 | Hughes CTD-UCSF-1 | 10 × 10 × 2mm$^3$ | Aquadhag/Aquadhag |

TABLE II
DETECTOR CHARACTERISTICS
(Single Photon Mode)

| Detector Code | Bias Voltage | Leakage Current | Energy Resolution Full-width-at-half maximum-height FWHM (at 60 Kev) | Peak to Plateau |
|---|---|---|---|---|
| A1 | 60V | 35 nA | 23.1% | 2.68 |
| A2 | 60V | 500 nA | 42.3% | 2.75 |
| A3 | 50V | 14 nA | 19.3% | 7.28 |
| AA4 Side 1 | 80V | 300 nA | — | 2.19 |
| Side 2 | 60V | 150 nA | — | 2.05 |
| AA5 Side 1 | 60V | 90 nA | — | 1.69 |
| Side 2 | 60V | 77 nA | — | 1.66 |
| A6 | 50V | 120 nA per element | — | — |
| B7 | 350V | 38 nA | 24.8% | 5.38 |

TABLE III
DETECTOR STABILITY
(Single Photon Mode)

| Detector Code | Leakage* Current Change | Photopeak* Shift (at 60 keV) | Peak to Plateau* Change (at 60 keV) |
|---|---|---|---|
| A1 | 35-50 nA | −0.56 keV | 2.68 → 2.67 |
| A2 | no change | no change | no change |
| A3 | no change | −10.5 keV | 7.28 → 4.22 |
| AA4 1 | breakdown | | |
| 2 | 220 → 260 nA | no change | 2.05 → 1.98 |
| AA5 1 | 90 → 110 nA | −1.6 keV | 1.69 → 1.61 |
| 2 | 77 → 89 nA | −0.8 keV | 1.66 → 1.58 |
| A6 | 120 → 170 nA | not measured | not measured |
| B7 | 38 → 40 nA | no change | 5.38 → 4.92 |

*Change over 15 minutes after the detector is under bias

As shown by Tables I-III the detectors were found to have initial leakage currents ranging from 14nA to 500nA, energy resolutions ranging from 19.3% to 42.3% and peak-to-plateau ratios (see FIG. 1) ranging from 7.28 to 1.66. Subsequent measurements showed that 15 minutes after the detectors were placed under bias, changes in leakage currents ranging from 0 to 50nA were evidenced, shifts in photo-peak ranged from 0 to −10 keV and the peak-to-plateau ratio evidenced changes ranging from 0 to almost 3.

Figure 7:
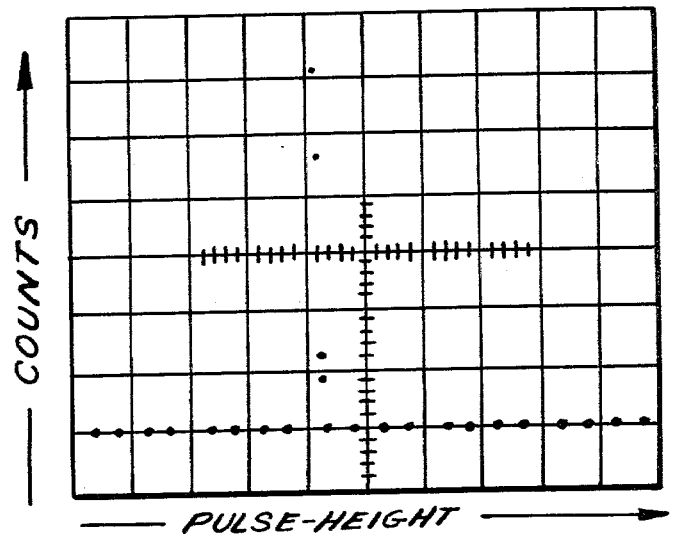
FIG. 7 is the spectral response of a CdTe detector used in accordance with the present invention.

The detectors were then tested in pulsed X-ray mode, in conjunction wth amplifier/filter 20A (FIG. 6), using X-ray pulse durations of approximately 100 μsec. and 800 μsec. Each of the detectors when used in cooperation with the amplifier 20A (FIG. 6) provided output signals with spectral responses such as that shown in FIG. 7, approaching the ideal impulse spectral response with no appreciable memory or tailing effects manifested.

The memory effects were tested by measuring the amplitude of a small pulse that was interlaced with a large pulse (approximately four times the amplitude of the smaller pulse). A wheel chopper was utilized to produce a pulsed beam with pulses occurring at intervals of approximately 20 msec., equivalent to the rate necessary for obtaining 1° increments of measurement in rotary CT scanner operating at a speed such that a 360° rotation is completed in 7.2 seconds. The large pulse was blocked with a synchronous second chopper to provide for observation of the change in measured amplitude of the smaller pulse. If the large memory effect observed in the uncompensated detector existed, a large shift would be manifested in the representation of the amplitude of the smaller pulse. However, no measurable shift was observed within a 1% measurement limit. Measurements were taken at 3.5 minute intervals over a period of 35 minutes. The results are summarized in Tables IV and V. The results demonstrate that after a short turn-on period, stable operation was attained by utilizing the pulsed source and circuit shown in FIG. 6, for measurement periods over approximately half an hour.

TABLE IV

DETECTOR STABILITY (PULSED MODE)

| Detector Code | Time to Stable Response | % Shift From Time Zero | Pulsed Width Used | No. of Pulses Per Event | Pulse % FWHM |
|---|---|---|---|---|---|
| A2 | 3.5 min.* | 4.6% | ~100μs | 20 | 2.5% |
|  | 3.5 min. | 2.9% | ~800μs | 20 | 2.8% |
| A3 | 10.5 min. | 6.2% | ~100μs | 20 | 4.0% |
|  | 10.5 min. | 6.7% | ~800μs | 20 | 3.8% |
| AA5 | 7.0 min. | 1.9% | ~100μs | 20 | 2.8% |
| A6 | 3.5 min.* | 0.5% | ~800μs | 10 | 4.6% |
| B7 | 3.5 min.* | 0.7% | ~100μs | 20 | 3.6% |

*NOTE:
Measurements made at 3.5 min. intervals

TABLE V

DETECTOR STABILITY (PULSED MODE)

| | OUTPUT (±.010) | | | | | |
|---|---|---|---|---|---|---|
| TIME (min.) | A2 * | + | A3 * | + | AA5 * | A6 + | B7 * |
| 0 | 1 | 1 | 1 | 1 | 1 | 1 | 1 |
| 3.5 | .954 | .971 | .967 | .973 | .997 | .993 | .995 |
| 7 | .960 | .970 | .945 | .933 | .982 | .993 | .999 |
| 10.5 | .969 | .974 | .938 | .917 | .988 | .992 | .978 |
| 14 | .970 | .972 | .937 | .896 | .987 | .991 | .979 |
| 17.5 | .975 | .968 | .937 | .876 | .985 | .995 | .990 |
| 21 | .984 |  | .938 | .855 | .977 | .981 | .997 |
| 24.5 | .982 |  |  | .849 | .980 | .971 | .997 |
| 28 | .985 |  |  | .857 | .986 | .979 | .992 |
| 31.5 | .982 |  |  |  | .981 | .980 | .973 |

TABLE V-continued

DETECTOR STABILITY (PULSED MODE)

| | OUTPUT (±.010) | | | | | |
|---|---|---|---|---|---|---|
| TIME (min.) | A2 * | + | A3 * | + | AA5 * | A6 + | B7 * |
| 35 | .984 |  |  |  |  | .990 | .984 |

* 100 μsec. pulse width
+ 800 μsec. pulse width

One of the problems with prior art usage of semiconductor detectors in general, the CdTe in particular, is the non-uniformity of the response exhibited between respective detectors, and, in addition, non-uniformity of response over the surface of a respective detector. The uniformity of response of the detectors when used in conjunction with a pulsed source and amplifier/filter 20 was checked, by collimating the X-ray source to a small area of the detector.

Figures 8, 9:
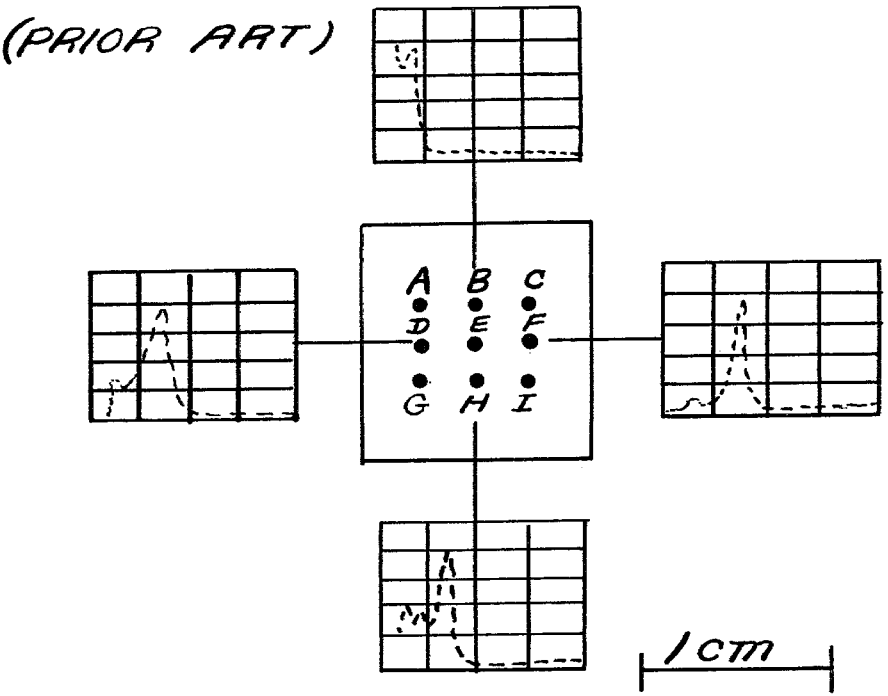
FIG. 8 illustrates the non-uniform response of a CdTe detector as used in the prior art.

Referring now to FIGS. 8 and 9, localized measurements were taken with the collimated radiation directed to various positions A–I on the detector surface. Such positions are illustrated in FIG. 8, along with spectral responses to a monochromatic source (AM-241) at various of those positions for the case of the most non-uniform detector (B7 in TABLES I–V) when used in accordance with the prior art. FIG. 9B shows the spectral response found at each of the positions A–I when the detector B7 was used in conjuction with a pulsed X-ray source and filtering amplifier 20. FIG. 9A more particularly indicates the normalized photo-peak response of the CdTe detector to collimated radiation at positions A–I using this invention.

It should be noted that while the CdTe detector has extremely non-uniform response when used in accordance with the prior art techniques, the deviations in response are of the order of ±2% when used in accordance with the present invention. More significantly, it was found that even using individual detectors of different geometry, (and in fact, made by different manufacturers) when the radiation source was collimated to provide equal irradiated areas, these detectors provided readings within 7% of each other when used in accordance with the present invention.

Figure 10A:
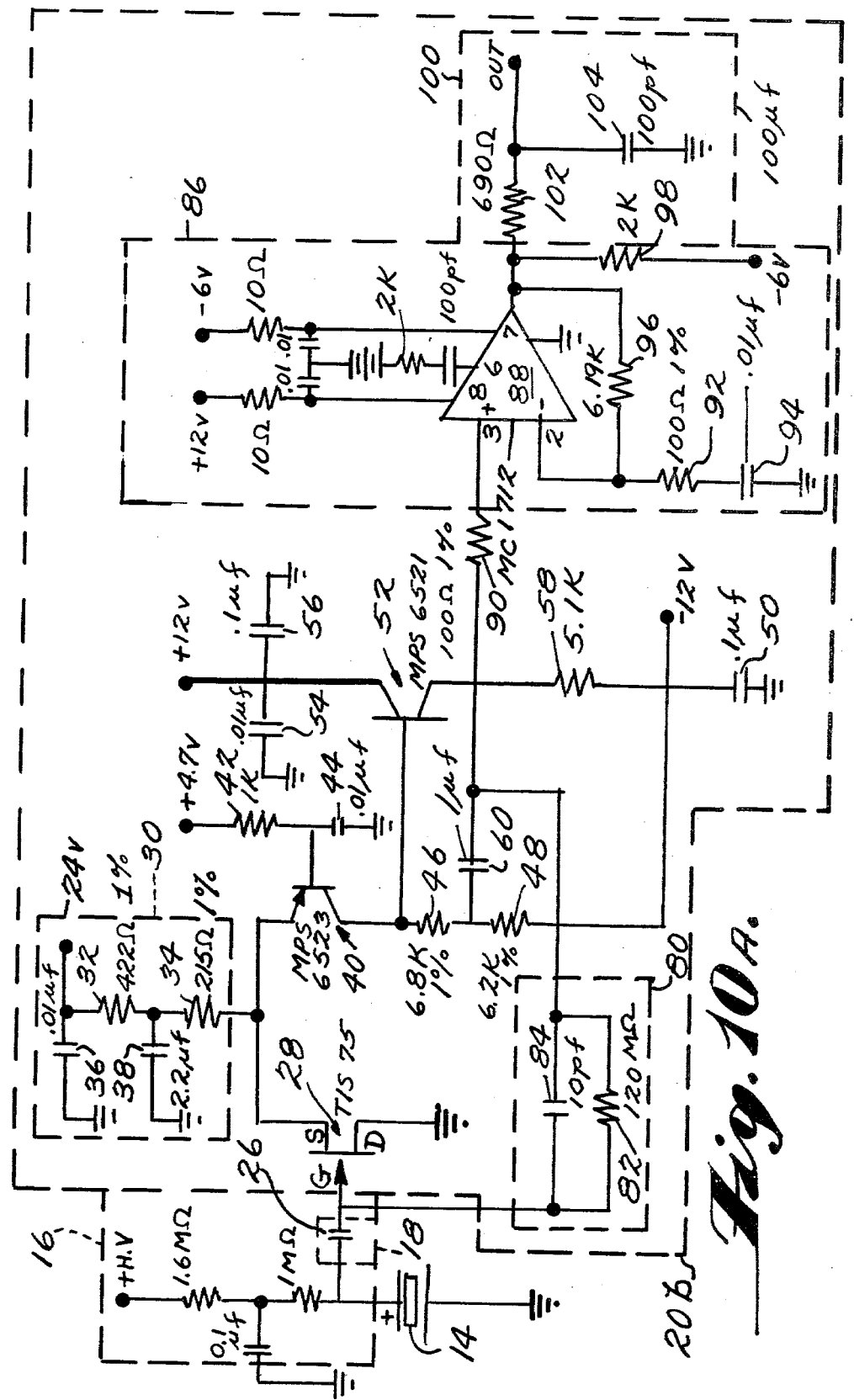
FIGS. 10A and 10B are schematic diagrams of alternative charge amplifier and filter means.

As noted above the amplifier/ filter 20B depicted in FIG. 10A also successfully compensates for the characteristics of detector 14. The exemplary component values here given are again suitable for operating with X-ray pulse durations on the order of 100 μsec. In the circuit of FIG. 10, FET 28 and transistors 40 and 52 are interconnected in the same manner as in FIG. 6, with the exception that fast differentiator 62 is replaced by long time constant circuit 80 comprising a parallel combination of a resistor 82 (120 MΩ), and capacitor 84 (10 pf.).

The emitter of transistor 52 is coupled to an active second stage 85. Active stage 85 comprises a differentiator portion 86 comprising an operational amplifier (op amp) 88, (e.g., of the type MC1712) and an integrator portion 100. The emitter of transistor 52 is coupled through a precision resistor 90, (100Ω) to a noninverting input of op amp 88. The inverting input of op amp 88 is coupled through a serially connected precision resistor 92 (100Ω) and capacitor 94 (0.01 μf.) to ground. Feedback from the output terminal of amplifier 88 to its inverting input is provided through a further precision resistor 96, (6.19KΩ). A connection from the output terminal of op amp 88 is made through a resistor 98 (2KΩ) to a −6 volt source. The output terminal of op amp 88 is also connected to an integrator 100 comprising a resistor 102 (690Ω) and a capacitor 104 (1000 pf.). Amplifier/filter 20B can be adapted for other radiation durations by changing the time constant of differentiator 86, integrator 100, and, where necessary, circuit 80. Similarly, for long pulse durations it may be necessary to adjust the effective time constant of biasing circuit 16 and coupling circuit 18.

Figure 10B:
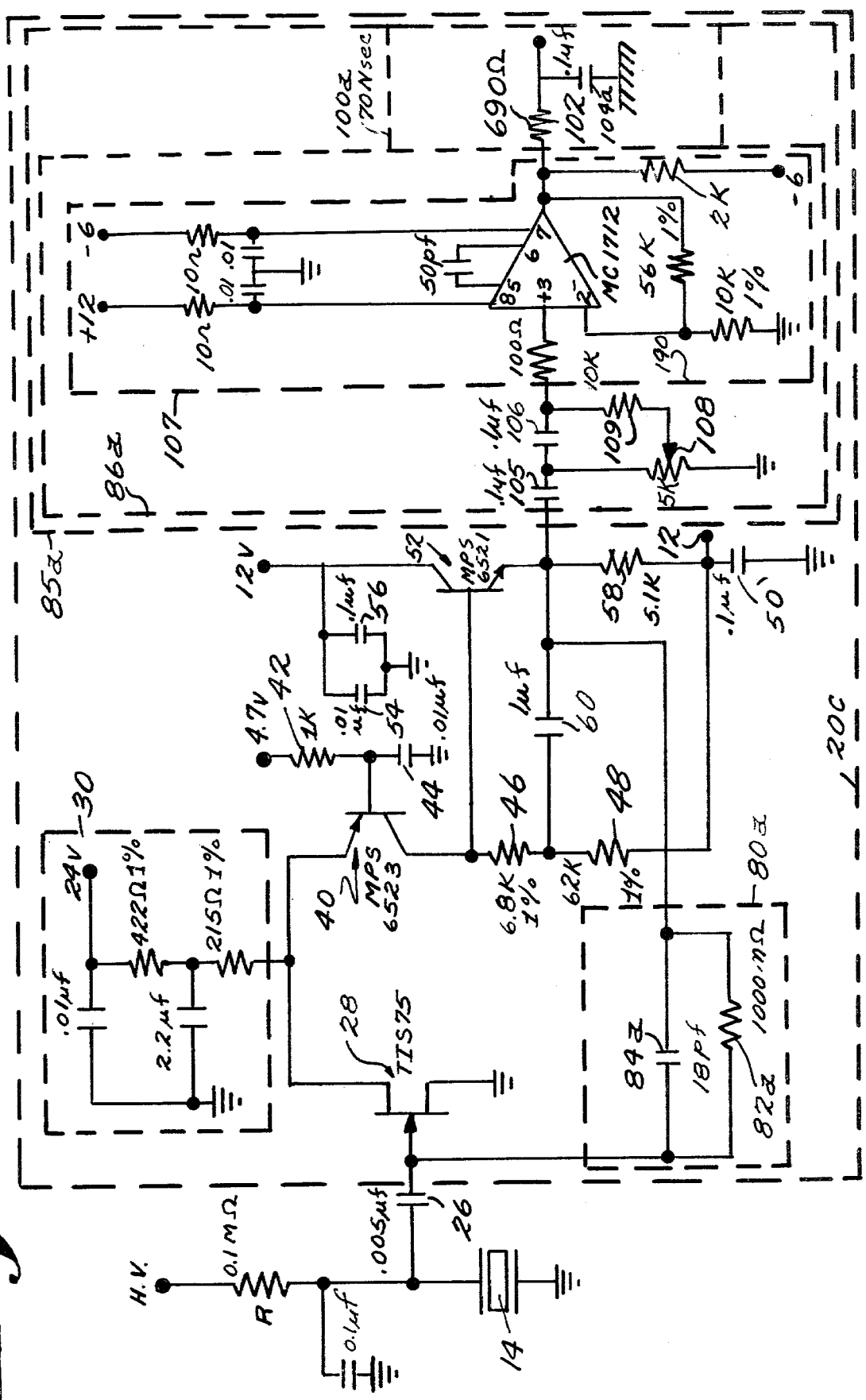

FIG. 10B depicts an amplifier/filter 20C similar to amplifier/filter 20B, but including provisions for pole zero compensation. The exemplary values given are again associated with a radiation pulse duration of on the order of 100 μs.

The long time constant circuit 80 of amplifier/filter 20B is replaced in amplifier/filter 20C by a long time constant circuit 80a of slightly different time constant, formed of a parallel combination of resistor 82a (1000MΩ) and capacitor 84a (18 pf). The emitter of transistor 52 is coupled through two serially connected capacitors 105 (1 μf) and 106 (1 μf) to the input of a voltage amplifier 107, suitably identical to voltage amplifier 67 in FIG. 6. A potentiometer 108 (5K) is connected between the juncture of capacitors 105 and 106 to ground potential. The wiper of potentiometer 108 is connected through a precision resistor 109 (10K) to the input of voltage amplifier 107. Capacitor 106 and resistor 109 cooperate to form an effective differentiator having time constant of 1ms.

Resistor 109 and capacitor 105 also cooperate with capacitor 105 and potentiometer 108 as a pole zero (p/z) compensation circuit.

The output of voltage amplifier 107 is connected to an integrator 100a, comprising a resistor 102 (690Ω) and capacitor 104a (0.1 [f). The time constant of integrator 100a is thus approximately 70 μs.

It should be appreciated that any of amplifier/filters 20A, 20B or 20C can be made compatible with faster pulse repetition frequencies by selectively discharging the capacitor (76, 104, 104a) of the integrator (68, 100, 100a) after the peak charge developed by detector 14 in response to a given radiation pulse has been attained. This can easily accomplished by shunting the conduction path of a transistor across the capacitor (76, 104, 104a) to ground, and controlling conduction through the transistor in accordance with the output signals of a conventional peak detector responsive to the output signal of the integrator.

As noted above, a conventional semiconductor detector such as CdTe or HgI2 can be made compatible with the requisites of CT scannning in accordance with the above described aspect of the present invention. As illustrated in the FIG. 11A, conventional semiconductor detectors comprise a wafer of the semiconductor material, (e.g. CdTe 110) having deposited on either side thereof conductive electrodes 112 and 114. The electrodes are typically formed of platinum or aquadhag.

Figures 11A, 11B, 11C, 11D:
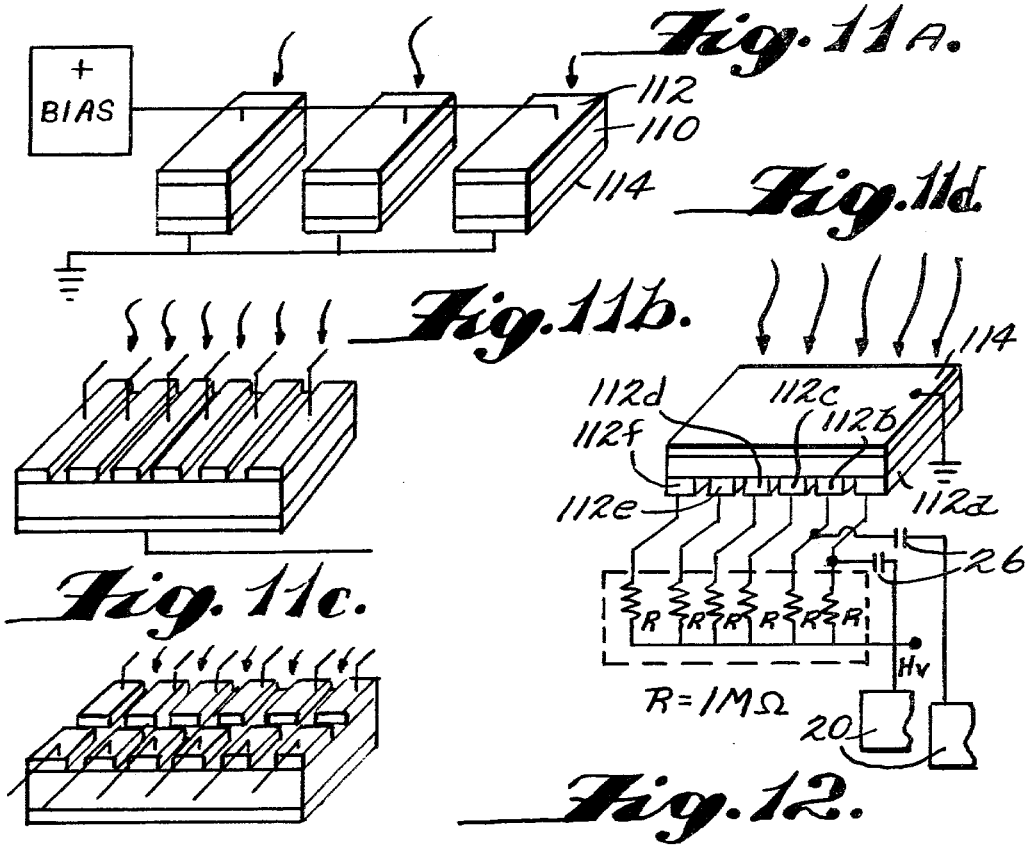
FIGS. 11A-11D are pictorial schematics of CdTe detectors in accordance with another aspect of the present invention.

Such unitary detector arrays are shown in FIGS. 11B and 11C. Assuming the incident radiation to scan across the detector in the longitudinal direction, an array of adjacent detectors can readily be provided by merely removing strips of electrode material in the transverse direction at longitudinally spaced locations to provide a plurality of electrically isolated electrodes FIG. 11B. Similarly, by additionally removing a strip of electrode material in the longitudinal direction (FIG. 11C) a two-dimensional array for simultaneously detecting multiple cross-sections in a CT scanner is provided.

In FIG. 11D a suitable biasing configuration is shown for such a multi-electrode detector. The detector is disposed such that it is irradiated by the X-ray pulses on its cathode (114) side, and individual anode electrodes 112a-112f are disposed on the far side of CdTe wafer 110. Cathode 114 is connected to ground potential and each individual anode connected to a high voltage source through a respective resistor, suitably of the value 1 MΩ. The high voltage source is on the order of 50 volts. Each anode is AC coupled through a respective capacitor 26 to an associated amplifier/filter 20.

It should be appreciated that radiation can also be directed to the anode side of the detector. Further, a unitary anode and plural cathodes could be utilized to form the unitary array. This is equivalent to connecting electrode 114 to the high voltage source and grounding each of the electrodes 112a-112f.

Figure 12:
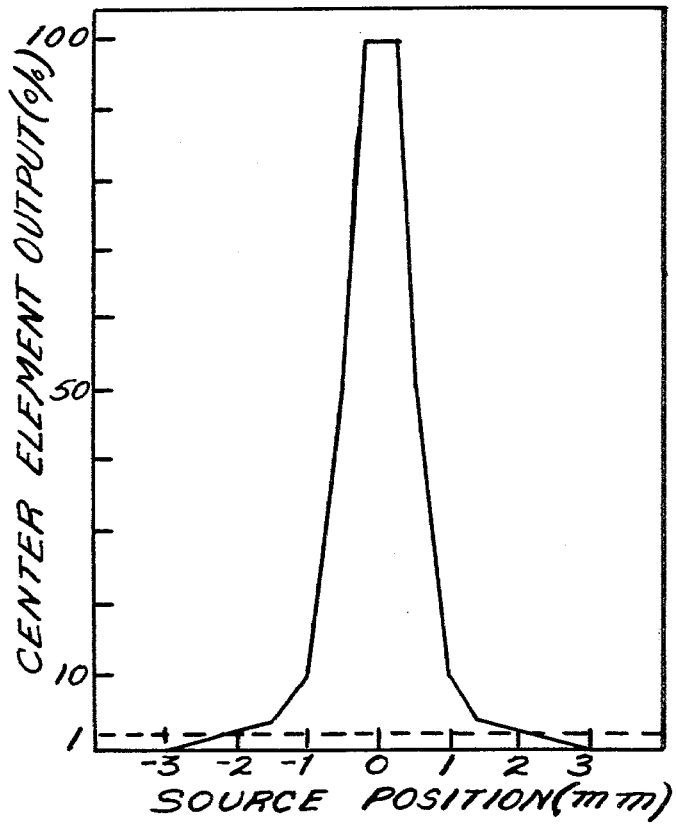
FIG. 12 illustrates the localized charge phenomenon of CdTe, and lack of crosstalk between elements in accordance with this invention.

Experiments show that crosstalk between the respective elements in the multi-element array of FIGS. 9B-9D are not appreciable. FIG. 12 illustrates the effect of scanning a narrow (1.5 mm) beam over one of the individual electrodes of such a detector, having one electrode per 2 mm in the direction of scanning. It appears that CdTe exhibits a localized charge property in response to incident radiation. When taking beam width into account, scattering effects within the detector contribute to less than 1% crosstalk at 1 mm. Such crosstalk produces an effect analogous to smoothing the data over the 1 mm range. If desired, a simple digital de-convolution procedure can be utilized, in effect, to unfold the data, and thus eliminate the inter-element crosstalk effect.

Figure 13:
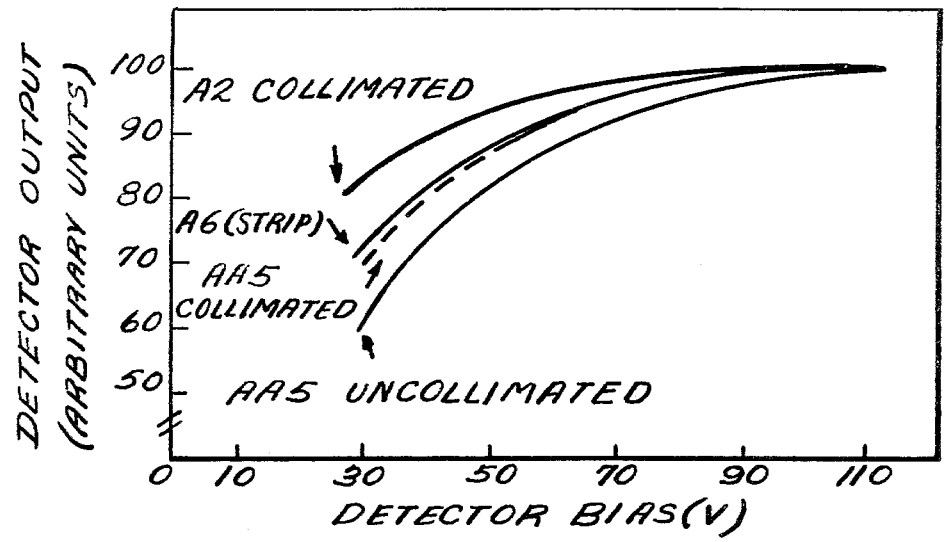
FIGS. 13 and 14 illustrate the charge response of CdTe detectors to bias voltage.
Figure 14:
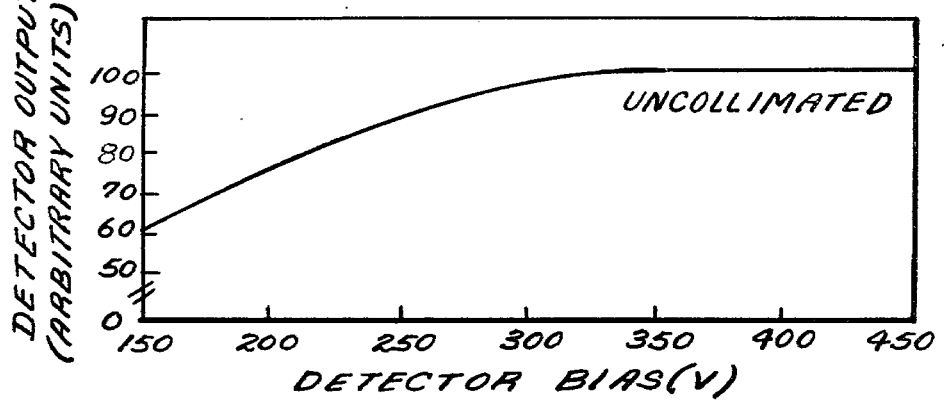

Measurements of the electrical pulse output of the detectors as a function of detector bias was performed to insure that all stopped photons contributed to the charge collected by the detector. It was found, as expected, that the response essentially flattens at high bias voltages where depletion is complete. Reference is made to FIGS. 13 and 14. It was also found that detectors with electrodes smaller than the detector area, in instances where the X-ray beam reaches the electrode edges, continue to yield larger pulses as the bias voltage is increased. This is apparently attributable to improved charge collection at the electrode edge. It was also found that where the incident radiation was collimated and only the central region of the electrode was irradiated, the detector output/detector bias response was the same as for the full coverage electrode detector.

It has also been determined that CdTe wafers only 2 mm thick provide adequate stopping power for CT scanning operations. Table VI shows the stopping power of a 2 mm CdTe wafer in cooperation with various pre-hardening radiation filters.

TABLE VI

| STOPPING POWER OF 2mm CdTe 150 kV X-RAY BEAM | |
|---|---|
| Prehardening Filter | Stopping Power |
| 6mm Al | 96% |
| 6mm Al, 1.3mm Cu | 93% |
| 6mm Al, 2.6mm Cu | 90% |
| 6mm Al, 3.9mm Cu | 89% |

Figure 15:
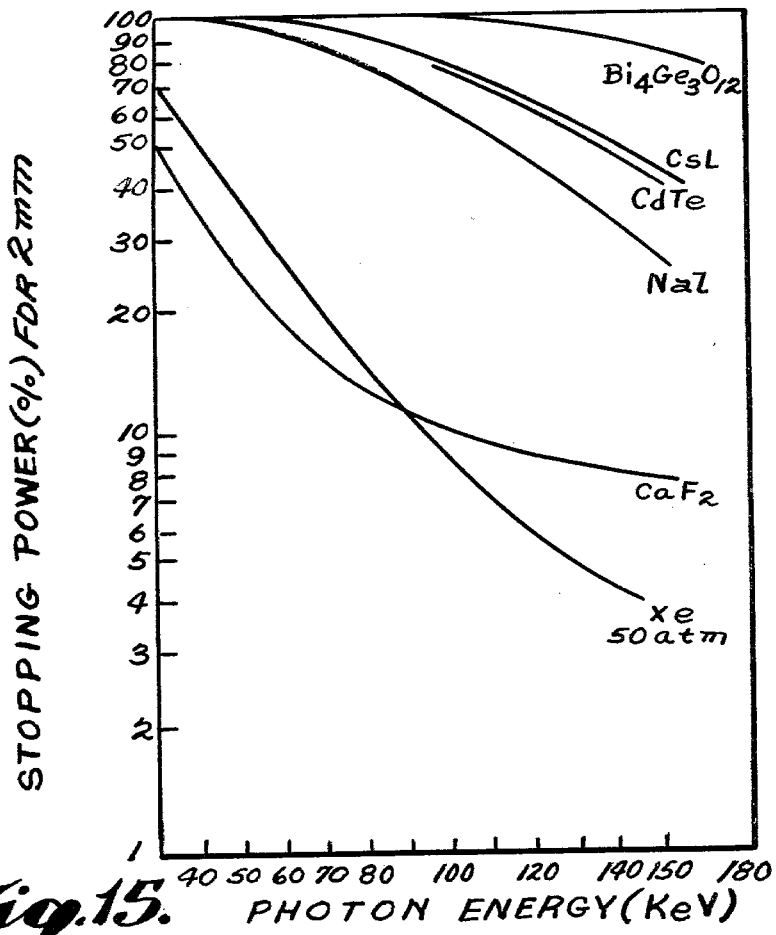
FIG. 15 compares the radiation stopping power of various detector materials.

FIG. 15 shows a comparison of the stopping powers of 2 mm thicknesses of various detector materials used in CT scanning (including scintillator crystals). It should be noted that while bismuth germanate has a high stopping power, it is a scintillator as opposed to being a direct electrical conversion material.

Figure 17:
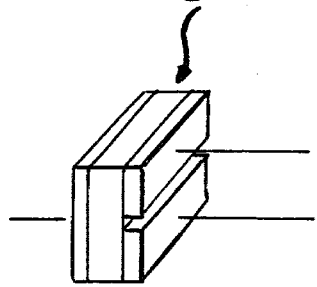
FIGS. 16 and 17 illustrate dual-energy detectors.
Figure 16:
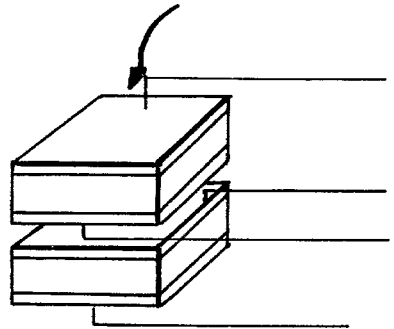

It is sometimes desirable to measure radiation occuring at more than one effective energy level. Measurements at different energies can be taken by disposing two detectors in the path of the radiation, such that radiation passing through the first detector is detected by the second, etc. as illustrated in FIG. 16. Such measurements can also be accomplished in accordance with one aspect of the present invention by disposing a multiple electrode detector, as shown in FIG. 17 such that the radiation is incident on a surface of the detector transverse to the electrodes. Here, the first electrode develops a charge in accordance with the number of photons passing through a given distance of CdTe and the second electrode develops a signal in accordance with the charge produced by the photons not blocked by the first portion of CdTe.

FIG. 18 illustrates the usage of this invention in a CT scanner. A plurality of multi-element detector arrays 14 (FIGS. 11B–11D) are disposed in a stationary circular array. A pulsed radiation source 24 provides a pulsed fan-shaped beam of radiation, which irradiates a body section 120 located in a patient circle 122. Source 24, is made to rotate about body section 120 to effect a 180°–360° scan. The radiation passing through body section 120 is detected by detectors 14. Each element of detector 14 is AC coupled, through associated means 18, to an associated amplifier/filter 20. The respective amplifier/filters are multiplexed by a conventional multiplexer 124 through an analog-to-digital converter 12 to suitable data processing circuitry 130. Data processing circuitry 130 may be any suitably programmed data processor or computer for reconstructing a point-by-point electron density profile of the scanned body section from the individual measurements. It should be appreciated that since only one group of detectors is irradiated at a given time, a number of detectors (each from a different mutually exclusive group), can be interconnected to share a given amplifier/filter 20. The scanning of the X-ray source itself effectively multiplexes respective interconnected detectors to a common amplifier/filter 20.

In summary, it has been found that when used in accordance with the present invention, room temperature semiconductor detectors such as CdTe, can be advantageously used in CT scanning. This involves use of a pulsed radiation source and an amplifier/filter which provides a processed output pulse from a predetermined range of frequency components present in the law detector poutput. The range of frequencies is chosen in accordance with the duration of the X-ray pulse. Such apparatus effectively removes the adverse properties of the detector as a factor in the overall performance. In effect, the pulse of incident radiation drives the rise-time response of the detector so that any adverse variatons in detector rise-times are not apparent in the final output signal from the detector electronics interface.

Further, it appears that CdTe detectors in particular, are especially advantageous. Electrodes appear to form only ohmic contacts with the CdTe wafer, without any appreciable boundary layer. The localized charge collection phenomenon also permits densely packed arrays of detectors to be formed on a single wafer by simple batch fabrication techniques. Densities of one detector per 2 millimeters have been defined on the face of a detector slab merely by scratching out sections of electrode material.

CdTe detectors are urged, easily handled and, when used in accordance with the present invention, very stable in electrical response. Since light pipes and PMT's are not needed, there is much more flexibility in designing detector configurations. For example, for dual energy detection, a thin CdTe detector (less than 0.5 mm thick) could be backed by a thicker, (2 mm) detector as shown in FIG. 16. Alternatively, a unitary configuration could be utilized such as shown in FIG. 17.

The same considerations that apply to CdTe also apply to HgI2. It is also thought that the following semiconductor materials among others, exhibit properties similar to those of CdTe and may be advantageously utilized in accordance with the present invention; gallium arsenide (GaAs), aluminum antimonide (AlSb), indium phosphate (InP), zinc telluride (ZnTe), tungsten selenide, (WSe$_2$), cadmium selenide (CdSe), bismuth iodide (BI$_3$) and cesium antimonide (Cs$_3$Sb). Similarly, germanium (Ge) of low quality typically exhibits properties not unlike those of CdTe.

While various conductors shown interconnecting the elements of some of the figures of the drawing are shown in single line form, they are not shown in a limiting sense and may comprise plural connections as is understood in the art. Nor should exemplary component values be construed in a limiting sense. The exemplary circuits can also be optimized for particular applications.

It should be further understood that the above description is of illustrative embodiments of the present invention, and that the invention is not limited to the specific forms shown. For example, while the present invention is described primarily in the environment of CT scanners, it should be appreciated that it may find application in other types of apparatus requiring the detection of radiation. Modifications may be made in the design and arrangement of the elements without departing from the invention as expressed in the appended claims.

We claim:

1. A radiation detecting apparatus for use in detecting incident radiation pulses of predetermined duration, said detector comprising:
   a semiconductor detector which generates electrical charge in response to incident radiation, said detector being disposed to receive at least a portion of said radiation pulses;
   signal processing means, AC coupled electrically to said semiconductor detector for generating an output electrical signal accurately representing said incident radiation,
   said signal processing means including filter means for allowing only frequency components within a predetermined range of frequencies to contribute to said output electrical signal, said range of frequencies being determined in accordance with the duration of said incident radiation pulses so that said output electrical signal is undistorted by variations in internal electrical characteristics of the semiconductor detector.

2. Apparatus of the type including (a) means for generating pulses of penetrating radiation having predetermined duration, (b) a detector disposed to receive a portion of said radiation, said detector exhibiting at least one of the adverse high current leakage, tailing, polarization, or memory properties, and (c) signal processing means responsive to electrical signals generated by the detector for providing an output electrical signal accurately representing the intensity of the radiation received by said detector, wherein:

said signal processing means is AC coupled to said detector and includes filter means for allowing only frequency components within a predetermined range of frequencies to contribute to said output electrical signal, said range of frequencies being in accordance with said radiation pulse duration so that distortion in said output signal due to said exhibited detector properties are substantially eliminated.

3. The apparatus of claims 1 or 2 wherein said signal processing means comprises:

an electrical charge amplifier having an input electrically coupled to said detector through a capacitor, a fast differentiator circuit connected in feedback relation with said charge amplifier; and an integrator responsive to the output of said charge amplifier.

4. The apparatus of claim 3 wherein said charge amplifier comprises a field effect transistor.

5. The apparatus of claims 1 or 2 wherein said signal processing means comprises:

a charge amplifier electrically coupled to said detector through a capacitor;

a differentiator responsive to the output signals of said charge amplifier; and an integrator responsive to the output of said differentiator.

6. The apparatus of claims 1 or 2 wherein said detector comprises a wafer of a material selected from the group of cadmium telluride and mercuric iodide having a cathode electrode in ohmic contact with one surface, and at least one anode contact in ohmic contact with an opposing surface of the wafer.

7. The apparatus of claim 6 wherein said detector includes a plurality of anode electrodes in ohmic contact with said wafer and electrically isolated from each other.

8. The apparatus of claim 7 wherein said detector is disposed with respect to said radiation source such that said radiation impinges upon a surface of said wafer transverse to said one surface, and said anode electrodes are respectively disposed such that they are at varying distance from said radiation source, whereby each anode provides signals corresponding to differing energies of incident radiation.

9. The apparatus of claims 1 or 2 further including a second semiconductor detector disposed to receive radiation passing through the first-referenced semiconductor detector.

10. The apparatus of claims 1 or 2 wherein said signal processing means for generating an output signal comprises:

a charge sensitive first stage having a first predetermined effective RC time constant; and a second stage, cooperating with said first stage, having a second predetermined effective RC time constant;

said first and second predetermined effective RC time constants being determined in accordance with the duration of said radiation pulse.

11. The apparatus of claim 10 wherein said first effective RC time constant is substantially less than the duration of said radiation pulse and said second effective RC time constant is on the same order as said pulse duration.

12. The apparatus of claim 10 wherein said first effective RC time constant is substantially greater than the duration of said radiation pulse and said second effective RC time constant is on the same order as said pulse duration.

13. The apparatus of claims 1 or 2 wherein said signal processing means for generating an output signal comprises:

a charge sensitive amplifier having a frequency response such that only frequencies within a predetermined band of frequencies centered about a frequency approximately equal to the inverse of the duration of said incident radiation pulses contribute to said output electrical signal.

14. The apparatus of claims 1 or 2 wherein said signal processing means for generating an output signal comprises:

a charge sensitive amplifier having a frequency response such that only frequencies within a predetermined band of frequencies centered about a frequency approximately equal to the inverse of twice the duration of said incident radiation pulses contribute to said output electrical signal.

15. The apparatus of claims 1 or 2 wherein said signal processing means comprises:

a charge amplifier electrically coupled to said detector through a capacitor;

a differentiator responsive to the output signals of said charge amplifier;

a voltage amplifier responsive to the output of said differentiator; and an integrator responsive to the voltage amplifier output.

16. A tomographic scanner for providing a plurality of radiation beam transmission/absorption measurements taken along each of plural paths with a cross-section of a three-dimensional body and for computing from such measurements the relative radiation absorptions occurring at incremental areas disposed within said cross-section, said tomographic scanner comprising:

means for generating a pulsed beam of said radiation, said beam pulses being of predetermined duration;

a semiconductor detector, disposed to receive said radiation after passage through said body, the raw output of said detector exhibiting undesirable electrical characteristics;

signal processing means, AC coupled to said detector, for generating an output signal accurately representing the amount of radiation incident on said detector;

said signal processing means including filter means for blocking signals for frequencies not within a predetermined range of frequencies from contributing to said output signal, said range of freequencies being determined in accordance with the duration of said radiation pulses so that said output signal is substantially undistorted by said undesirable characteristics of said detector;

means for effecting a change in the geometric relationship between at least two of said radiation beam, detector, or body, such that said detector receives radiation from along a plurality of different paths through said body; and data processing means, receptive of said output signal for computing said relative radiation absorptions.

17. The tomographic scanner of claim 16 wherein said detector comprises a wafer of cadmium telluride having a cathode electrode in ohmic contact with one surface, and at least one anode contact in ohmic contact with a surface opposite said one surface.

18. The tomographic scanner of claim 17 wherein said detector includes a plurality of anode electrodes ohmically contacted to said wafer and electrically isolated from each other.

19. The tomographic scanner of claim 18 wherein said detector is disposed with respect to said radiation source such that said radiation impinges upon a surface of said wafer transverse to said one surface and to said opposite surface, and said respective electrodes are disposed such that they are at varying distances from said radiation source so that each anode provides signals representing differing effective energies of incident radiation.

20. In a tomographic scanner of the type including (a) a source of penetrating radiation, (b) radiation detectors disposed for detecting the radiation after passage through the body along different paths, and (c) data processing means for computing relative radiation absorptions at incremental areas within a cross-section of the body, the improvement wherein:
said source includes means for generating pulses of said radiation, said pulses having a predetermined duration; and
said detectors comprise a wafer of cadmium telluride having fist and second opposing surfaces with one of said opposing surfaces having a cathode electrode disposed thereon and the other of said opposing surfaces having at least one anode electrode disposed thereon;
means for developing a bias voltage across said wafer;
signal processing means, AC coupled to one of said electrodes, for generating an output signal accurately representing radiation incident on the detector, said signal processing means including filter means allowing only signal components from said detector within a predetermined range of frequencies to contribute to said output signal, said range of frequencies being determined to accordance with the duration of said radiation pulse so that the output signal provides an accurate representation of the incident radiation undistorted by adverse internal electrical characteristics of said cadmium telluride wafer.

21. The tomographic scanner of claim 20 wherein said wafer includes a plurality of said anode electrodes electrically isolated from each other;
each said anode being AC coupled to an associated one of said signal processing means.

22. The tomographic scanner of claims 16 or 20 wherein said signal processing means comprises:
a charge amplifier having an input coupled to said detector through a capacitor;
a fast differentiator circuit connected in feedback relation with said charge amplifier; and
an integrator responsive to the output of said charge amplifier.

23. The tomographic scanner of claim 22 wherein said charge amplifier comprises a field effect transistor.

24. The tomographic scanner of claims 16 or 20 wherein said signal processing means comprises:
a charge amplifier coupled to said detector through a capacitor;
a differentiator responsive to the output of said charge amplifier; and
an integrator responsive to the output of said differentiator.

25. The tomographic scanner of claims 16 or 20 further including a second semiconductor detector disposed to receive any radiation passing through said first-references semiconductor detector.

26. The tomographic scanner of claims 16 or 20 wherein said signal processing means comprises:
a charge sensitive first stage having a first predetermined effective RC time constant; and
a second stage, cooperating with said first stage, having a second predetermined effective RC time constant;
said first and second predetermined effective RC time constants being determined in accordance with said radiation pulse duration.

27. The tomographic scanner of claim 26 wherein said first effective RC time constant is substantially less than said radiation pulse duration and said second effective RC time constant is on the same order as said pulse duration.

28. The tomographic scanner of claim 26 wherein said first effective RC time constant is substantially greater than said radiation pulse duration and said second effective RC time constant is on the same order as said pulse duration.

29. The tomographic scanner of claims 16 or 20 wherein said signal processing means comprises:
a charge sensitive amplifier having a frequency response such that only frequencies within a predetermined band of frequencies centered about a frequency approximately equal to the inverse of the duration of said incident radiation pulses contribute to said output electrical signal.

30. The tomographic scanner of claims 16 or 20 wherein said signal processing means comprises:
a charge sensitive amplifier having a frequency response such that only frequencies within a predetermined band of frequencies centered about a frequency approximately equal to the inverse of twice the duration of said incident radiation pulses contribute to said output electrical signal.

31. The tomographic scanner of claims 16 or 20 wherein said signal processing means comprises:
a charge amplifier coupled to said detector through a capacitor;
a differentiator responsive to the output of said charge amplifier;
a voltage amplifier responsive to the output of said differentiator; and
a integrator responsive to the output of the voltage amplifier.

32. An apparatus for measuring the intensity of incident radiation pulses having a predetermined duration, said apparatus comprising:
a wafer of a material selected from the group consisting of CdTe and HgI2 having first and second surfaces defining a predetermined thickness;
a first conductive layer deposited on said first surface;
a second conductive layer deposited on said second surface, said second conductive layer including a plurality of individual electrically isolated sections, each serving as a separate electrode to said wafer, whereby a plurality of individual detectors are provided on said wafer; and a plurality of signal processing means each respectively electrically coupled to a corresponding one of said separate electrodes, for detecting and processing electrical signals presented at said electrodes and for providing output signals accurately representing the intensity of radiation incident on each detector.

33. The detector of claim 32 wherein said predetermined thickness is approximately 2 mm.

34. The detector of claims 32 or 33 wherein said individual electrically isolated sections are disposed on said second surface such that the center of adjacent centers are relatively disposed at approximately 1 mm intervals or less along the length of said second surface.

35. The detector of claims 32 or 33 wherein a plurality of said individual isolated sections are disposed along the width of said second surface.

36. In an apparatus for providing a measurement of radiation transmission/absorption by a cross-section of a body disposed between a pulsed radiation source and a detector, an improved detector comprising:

a wafer of CdTe, having a surface disposed towards said source;

a first conductive layer disposed on a first surface of the wafer and serving as a first electrode to said wafer;

a plurality of individual electrically separate conductive layers disposed on another surface of the wafer, said plurality of layers being spaced apart along the length of said second surface and each serving as an electrode to said wafer, whereby an array of individual detectors is provided on said wafer; and signal processing means AC coupled to each of said plurality of conductive layers for processing the electrical signals presented thereat and for providing corresponding plural output signals which are substantially accurate representations of the radiation incident on each corresponding individual detector.

37. The detector of claim 36 wherein said individual electrically isolated layers are disposed on said second surface such that adjacent centers are spaced apart at approximately 1 mm intervals or less along the length of said second surface.

38. Apparatus for providing a measurement of relative radiation transmission/absorption by a body, said apparatus comprising:

means for generating pulses of radiation, said pulses being of a predetermined duration and being directed to irradiate said body;

detector means, disposed to receive at least a portion of the radiation pulses transmitted through said body, for accumulating an electrical charge in response to said transmitted radiation incident thereon, said charge accumulation being a function of varying time response characteristics within the detector means; and charge sensitive amplifier and frequency filter means, for generating an output electrical signal in response to said accumulated charge which is substantially independent of said varying time response characteristics.

39. The apparatus of claim 38 wherein said detector means comprises a semiconductor detector.

40. The apparatus of claims 38 or 39 wherein said charge sensitive amplifier and frequency filter means comprises:

a charge amplifier having an input coupled to said detector through a capacitor;

a fast differentiator circuit connected in feedback relation with said charge amplifier; and an integrator responsive to the output signals of said charge amplifier.

41. The apparatus of claim 40 wherein said charge amplifier comprises a field effect transistor.

42. The apparatus of claims 38 or 39 wherein said charge sensitive amplifier and frequency filter means comprises:

a charge amplifier coupled to said detector through a capacitor;

a differentiator responsive to the output signals of said charge amplifier; and an integrator responsive to the output of said differentiator.

43. The apparatus of claims 38 or 39 wherein said detector means comprises a wafer of cadmium telluride having a first electrode in contact with a first surface thereof, and at least one second electrode in contact with a second surface.

44. The apparatus in claim 43 wherein said detector means includes a plurality of said second electrodes contacted to said wafer and electrically isolated from each other.

45. The apparatus of claim 44 wherein said detector means is disposed with respect to said radiation source such that said radiation impinges upon a third surface of said wafer transverse to said first and second surfaces, and respective ones of said second electrodes are disposed at respectively varying distances from said radiation source so that each second electrode provides signals at differing effective energies of incident radiation.

46. The apparatus of claim 44 wherein said detector means includes a second CdTe detector disposed to receive radiation passing through said first-references CdTe detector.

47. The apparatus of claims 38 or 39 wherein said charge sensitive amplifier and frequency filter means comprises:

a charge amplifier coupled to said detector through a capacitor;

a differentiator responsive to the output signals of said charge amplifier;

a voltage amplifier responsive to the output of said differentiator; and an integrator responsive to the output of the voltage amplifier.

48. A method for detecting incident radiation pulses of predetermined duration, comprising the steps of:

disposing a semiconductor detector to receive at least a portion of said radiation, said semiconductor detector generating an electrical charge in response to said received radiation;

generating an electrical output signal indicative of said charge; and filtering out components of said electrical output signal not in accordance with the duration of said radiation pulses so that said electrical output signal is substantially undistorted by characteristics of said semiconductor detector.

49. An apparatus for measuring the intensity of incident radiation pulses having a predetermined duration, said apparatus comprising:

a wafer of material selected from the group of CdTe and HgI2 having first and second surfaces defining a predetermined thickness;

a first conductive layer deposited on said first surface; and a second conductive layer deposited on said second surface, said second conductive layer including a plurality of individual electrically isolated sections, each serving as a separate electrode to said wafer, whereby a plurality of individual detectors are provided on said wafer.

50. The detector of claim 49 wherein said predetermined thickness is approximately 2 mm.

51. The detector of claims 49 or 50 wherein said individual electrically sections are disposed on said second surface such that the center of adjacent centers are relatively disposed at approximately 1 mm intervals or less along the length of said second surface.

52. The detector of claims 49 or 50 wherein a plurality of said individual isolated sections are disposed along the width of said second surface.

53. In an apparatus for providing a measurement of radiation transmission/absorption by a cross-section of a body disposed between a pulsed radiation source and a detector, an improved detector comprising:

a wafer of a material selected from the group consisting of CdTe and HgI2 having a surface disposed towards said source;

a first conductive layer disposed on a first surface of the wafer and serving as a first electrode to said wafer; and a plurality of individual electrically separated conductive layers disposed on a second surface of the wafer, said plurality of layers being spaced apart along the length of said second surface, each serving as an electrode to said wafer, whereby an array of individual detectors is provided on said wafer.

54. The detector in claim 53 wherein said individual electrically isolated layers are disposed on said second surface such that adjacent centers are spaced apart at approximately 1 mm intervals or less along the length of said second surface.

55. A method for providing a measurement of radiation transmission-absorption by a cross-section of a body, comprising the steps of:

generating pulses of radiation of predetermined duration;

directing said radiation pulses to irradiate said body;

disposing a semiconductor detector to receive at least a portion of said radiation transmitted through said body, said semiconductor detector generating an electrical charge in response to said received radiation;

generating an electrical output signal indicative of said charge; and filtering out components of said electrical output signal not in accordance with the duration of said radiation pulses so that said electrical output signal is substantially undistorted by characteristics of said semiconductor detector.

56. A method for providing a measurement of radiation transmission/absorption by a cross-section of a body, comprising the steps of:

generating pulses of radiation of predetermined duration;

directing said radiation pulses of irradiate said body;

disposing a wafer of material selected from the group of CdTe and HgI2 to receive at least a portion of said radiation transmitted through said body;

disposing on one side of said wafer a plurality of spaced apart electrodes and on an opposing surface a common electrode, respective electrical charges being developed between said plurality of electrodes and said common electrode;

generating respective electical output signals indicative of said respective electrical charges; and filtering said respective electrical output signals to develop respective filtered electrical output signals having only frequency components within a predetermined range of frequencies in accordance with the duration of said radiation pulses; and processing said filtering electrical output signals to provide an accurate representation of the intensity of the radiation.

57. A method for using in an apparatus for measuring relative radiation transmission/absorption of a body a radiating detector having at least one of the adverse properties of high current leakage, tailing, polarization, or memory properties, comprising the steps of:

directing pulses of radiation to irradiate said body, said pulses being of predetermined duration;

disposing said radiation detector to receive at least a portion of said radiation transmitted through said body, said radiation detector generating an electrical charge in response to said received radiation;

generating an electrical output signal indicative of said electrical charge;

filtering said electrical output signal to develop a filtered output signal containing only frequency components within a range of frequencies in accordance with said predetermined duration of said radiation pulse such that frequency components associated with said adverse properties of said detectors are substantially eliminated from said filtered output signal; and processing said filtered output signal to provide an accurate representation of said transmission/absorption.

58. A method for providing simultaneous measurements of radiation transmission/absorption in a plurality of adjacent cross-sections of a body, comprising the steps of:

directing pulses of radiation to irradiate said respective cross-sections;

disposing a wafer of material selected from the group of CdTe and HgI2 having disposed on one surface thereof a plurality of spaced apart electrodes and on an opposing surface a common electrode, such that each of said plurality of electrodes receives a radiation transmitted through a respective one of said cross-sections, and develops a respective electrical charge in said wafer in accordance with said received radiation;

generating respective electrical output signals indicative of said respective electrical charges; and filtering said respective electrical output signals to develop respective filtered electrical output signals having only frequency components within a predetermined range of frequencies in accordance with the duration of said radiation pulses; and processing said respective filtered electrical output signals to provide respective representations of the transmission/absorption of said respective cross-sections.

59. A method for providing simultaneous measurements of radiation transmission/absorption of a body at a plurality of effective energy levels, comprising the steps of:

directing pulses of radiation to irradiate said body, said pulses being of predetermined duration;

disposing a wafer of material selected from the group of CdTe and HgI2 having a common electrode on one opposing surface, such that at least a portion of said radiation pulse transmitted through said body is incident on a surface of said wafer transverse to said one surface and said opposing surface to develop respective charges between said plural electrodes and said common electrode in accordance with the intensity of the radiation passing into the region of said wafer between respective ones of said plurality of electrodes and said common electrode;

disposing on one side of said wafer a plurality of spaced apart electrodes and on an opposing surface a common electrode, respective electrical charges being developed between said plurality of electrodes and said common electrode;

generating respective electrical output signals indicative of said respective electrical charges; and filtering said respective electrical output signals to develop respective filtered electrical output signals having only frequency components within a predetermined range of frequencies in accordance with the duration of said radiation pulses; and processing said respective filtered electrical output signals to provide accurate representations of said radiation transmission/absorption at the energy levels associated with said radiation passing through respective distances of CdTe.

* * * * *